US00PP34352P3

(12) United States Plant Patent
Kenworthy

(10) Patent No.: US PP34,352 P3
(45) Date of Patent: Jun. 14, 2022

(54) ZOYSIAGRASS PLANT NAMED 'FAES1307'

(50) Latin Name: ***Zoysia japonica* x *matrella***
Varietal Denomination: FAES1307

(71) Applicant: Florida Foundation Seed Producers, Inc., Marianna, FL (US)

(72) Inventor: Kevin E. Kenworthy, Gainesville, FL (US)

(73) Assignee: FLORIDA FOUNDATION SEED PRODUCERS, INC, Marianna, FL (US)

( * ) Notice: Subject to any disclaimer, the term of this patent is extended or adjusted under 35 U.S.C. 154(b) by 0 days.

(21) Appl. No.: 17/157,899

(22) Filed: Jan. 25, 2021

(65) Prior Publication Data

US 2021/0315143 P1 Oct. 7, 2021

Related U.S. Application Data

(60) Provisional application No. 62/966,446, filed on Jan. 27, 2020.

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./384, 390
See application file for complete search history.

(56) References Cited

U.S. PATENT DOCUMENTS

PP11,466 P 8/2000 Ito et al.
PP13,166 P2 11/2002 Doguet
PP27,051 P3 8/2016 Chapman

OTHER PUBLICATIONS

Buck, B. Dec. 17, 2019. Featured UF/IFAS Cultivars released in 2019 include Fruits, Oat and Zoysiagrass. UP/IFAS Blogs. http://blogs.ifas.ufl.edu/news/2019/12/17/featured-uf-ifas-cultivars-released-in-2019-include-fruits-oat-and-zoysiagrass/. 7 pgs. (Year: 2019).*

* cited by examiner

*Primary Examiner* — Karen M Redden
(74) *Attorney, Agent, or Firm* — Dentons US LLP

(57) ABSTRACT

'FAES1307' is a new and distinct zoysiagrass (*Zoysia japonica* Steud.) variety distinguished at least by its smooth leaf texture with occasional fine hairs on the upper surface, high turfgrass quality, good drought tolerance, improved winter turfgrass color retention, and low incidence of large patch disease caused by *Rhizoctonia solani* anastomosis group 2-2 LP. Compared to its parents and commercial checks, 'FAES1307' has a shorter canopy height and is a more prolific producer of stolons. It tends to have shorter leave lengths and moderate leaf widths. Its flag leaf height is similar to its female parent, 'FAES 5309-12' while its flag leaf width is similar to its male parent, 'BA 123'. The seed head heights of 'FAES1307' are shorter and consistent with the height of its female parent, 'TAES 5309-12'. 'FAES1307' and its parents have narrower raceme widths; and shorter raceme lengths compared to to 'Meyer' and 'SS-500'.

3 Drawing Sheets

ACKNOWLEDGEMENT OF FEDERAL RESEARCH SUPPORT

This invention was made with government support under 2015-51181-24291 awarded by the National Institute of Food and Agriculture, United States Department of Agriculture (U.S.D.A.). The government has certain rights in the invention.

Latin name of the genus and species of the plant claimed: *Zoysia japonica* x *matrella.*

Variety denomination: 'FAES1307'.

BACKGROUND OF THE INVENTION

The present invention relates to a new and distinct perennial zoysiagrass variety (*Zoysia japonica* x *Z. matrella*) designated 'FAES1307'. 'FAES1307' is an $F_1$ hybrid that was produced in Gainesville, Fla. in 2007 by crossing 'TAES 5309-12' (not patented *Z. japonica* Steud), as the female parent, with 'BA 123' (not patented *Z. matrella* (L.)

Merr.), as the male parent. 'FAES1307' was first asexually propagated in Gainesville, Fla. in 2008 by obtaining vegetative cuttings of stolons, tillers, or rhizomes, each with a vegetative bud, and rooting them in potting media. Asexually reproduced plants of 'FAES1307' have remained stable and true to type through at least 6 successive cycles of vegetative propagation. 'FAES1307' has been determined to be tetraploid (2n=4x=40). Compared to its parents, 'FAES1307' most closely resembles 'TAES 5309-12'.

SUMMARY OF THE INVENTION

'FAES1307' is a perennial zoysiagrass that spreads by stolons and rhizomes and was identified in 2017 in view of its superior attributes from a collection of zoysiagrass plants that were evaluated for turfgrass quality traits in Citra, Fla. under cultivated conditions. 'FAES1307' can be unambiguously distinguished based on its medium leaf texture, overall high turfgrass quality based on multiple experiments in Florida, good shade tolerance, high turfgrass sod strength, and low incidence of large patch disease caused by *Rhizoctonia solani* anastomosis group 2-2 LP. 'FAES1307' may be used as a turfgrass that is suitable for home lawns and commercial turf applications. The observed turfgrass quality and high turfgrass sod strength of 'FAES1307' should provide an alternative zoysiagrass cultivar for use across the southern and central areas of the U.S. zoysiagrass adaptation zone. Additionally, 'FAES1307' should be equally well-suited to other subtropical and tropical areas worldwide where zoysiagrass cultivars are currently grown.

BRIEF DESCRIPTION OF THE DRAWINGS

This new zoysiagrass plant is illustrated by the accompanying photograph of approximately six month old plants grown in a greenhouse in Gainesville, Fla., as provided in FIGS. 1 and 2. These photographs show the plant's typical form, foliage, and inflorescence. The colors shown are as true as can be reasonably obtained by conventional photographic procedures.

DETAILED BOTANICAL DESCRIPTION

Figure 1:
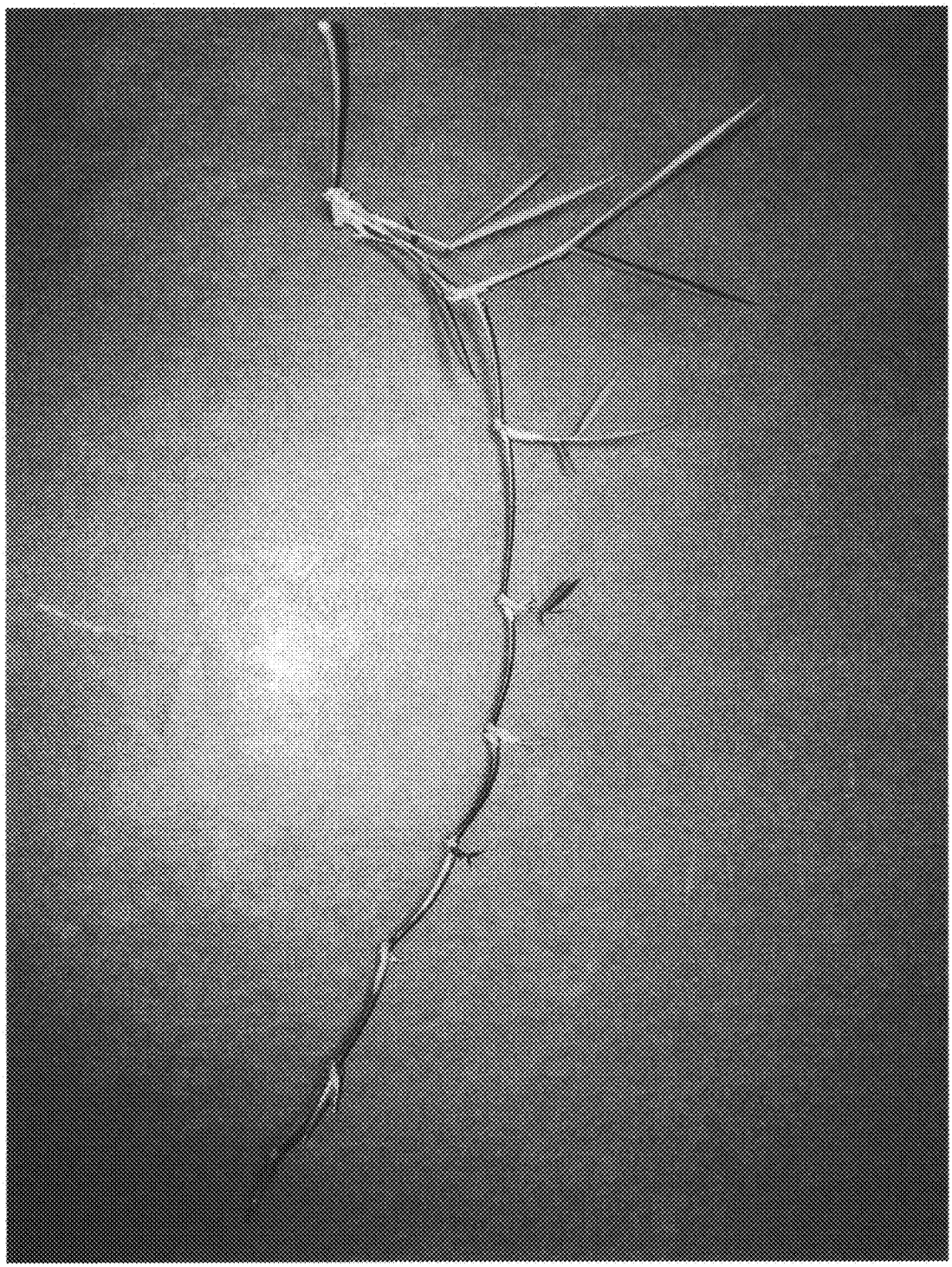
FIG. 1—Shows a tiller of the claimed plant.
Figure 2:
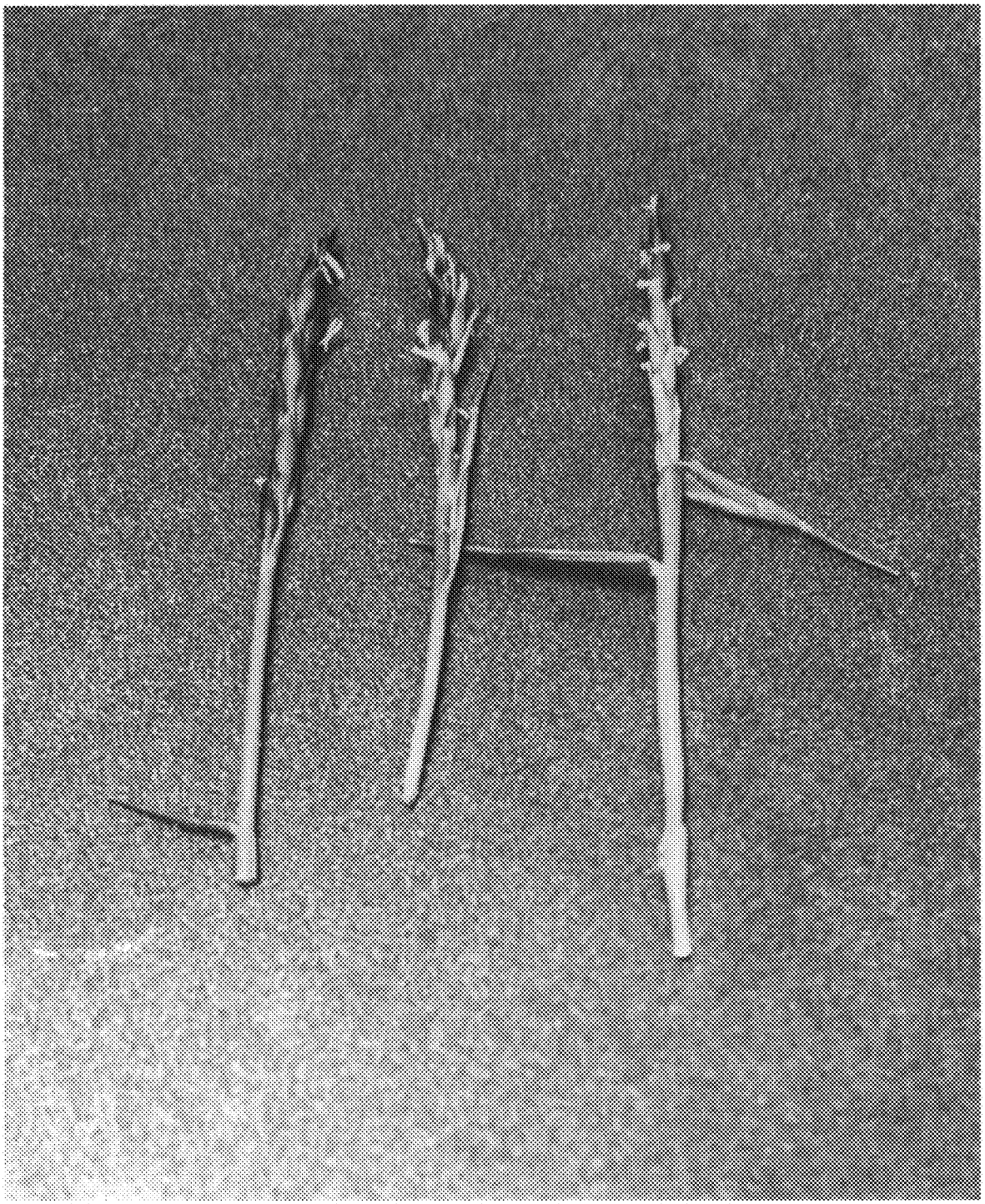
FIG. 2—Shows the inflorescence of the claimed plant

The following detailed description sets forth distinctive characteristics of 'FAES1307', as characterized in greenhouse and field conditions. The detailed description was obtained using approximately six month old plants grown in a greenhouse in Gainesville, Fla. Rooted plant material from asexual propagations was used as planting stock for studying performance in field plots and for greenhouse comparisons of morphological characteristics. 'FAES1307' has not been observed under all possible environmental conditions, and the measurements given may vary when grown in different environments. Certain characteristics may also vary with plant age. The color descriptions provided herein are based on The Royal Horticultural Society (R.H.S.) Colour Chart by The Royal Horticultural Society, London, Sixth Revised Edition. If any R.H.S. color designations below differ from the accompanying photographs, the R.H.S. color designations are accurate. Botanical assessments were obtained in Gainesville, Fla.

Morphological Comparison of 'FAES1307' to Commercial and Experimental Genotypes The morphological characteristics of 'FAES1307' were compared to its parents ('TAES 5309-12', *Z. japonica* and 'BA 123', *Z. matrella*) and commercial cultivars ('SS-500', U.S. Plant Pat. No. 11,466P; 'Zeon', U.S. Plant Pat. No. 13,166P2; 'Emerald' (not patented); and 'Meyer'). Comparative measurements were made using greenhouse grown plants in 8.9 cm diameter pots. The pots were planted in October 2019 using five sprigs per pot and allowed to fully establish prior to measurements. The greenhouse environment ranged from nighttime lows of 60° F. and daytime highs of 90° F. Plants were grown under natural lighting and fertilized using a soluble fertilizer of 20-20-20 in four equal applications per month, equating to one pound of nitrogen per month. The pots were arranged in a randomized complete block design with two runs of measurements made in 2020. Run one contained six replications with measurements taking place by rep from 29 April to 6 May 2020. Run two contained five replications with measurements taking place by rep from 7 October to 9 October. For both runs, pots were last trimmed two months before measurements. Pots were trimmed to a canopy height of 5.0 cm and stolons were trimmed back to the pot edge.

The number of stolons were counted for each pot and canopy height was measured from the soil surface to the tallest leaf blades. Subsequently, three stolons were randomly removed from each pot. Using these stolons, stolon length was measured, the leaf length and width from the most mature leaf arising from the first node (oldest node) of the removed stolon were measured. For flowering traits, three subsamples from each pot were measured and included flag leaf height, seed head height, and culm length measured from the soil surface. Additionally, flag leaf width, raceme width and length were measured, and the number of spikelets counted.

'FAES1307' had the shortest canopy height in run one and the second shortest in run two (Table 1). Its canopy heights were similar to 'Emerald' and 'Zeon' in run one, and with 'Emerald' in run two. In both runs, the canopy height of 'FAES1307' was shorter than 'Meyer', 'SS-500', 'BA 123', and 'TAES 5309-12'. 'FAES1307' produced the most stolons in each run. In run one 'FAES1307' was alone in the top statistical group; however, stolon numbers of 'Zeon' and 'TAES 5309-12' were similar in run two. 'FAES1307' always produced more stolons than 'SS-500', 'BA 123', 'Meyer', and 'Emerald'. For stolon length, 'FAES1307' had the longest stolons compared to all other entries in run one. However, in run two, the stolon length of 'FAES1307' was not different from any other entries (Table 1).

The leaf length of 'FAES1307' tended to be shorter but comparisons were not consistent between runs (Table 1). In run one, 'FAES1307' was only different from 'Meyer' which had the longest leaves. In run two, 'SS-500' had longer leaves, whereas 'Emerald' and 'BA 123' had shorter leaves. The leaf lengths of 'FAES1307', 'TAES 5309-12', and 'Zeon' were not different in either run. The leaf width of 'FAES1307' was moderate among the compared genotypes in both runs. In both runs, 'Emerald', 'Zeon', and 'BA 123' had narrower leaf widths, and 'Meyer' and 'SS-500' had longer leaf widths. Leaf widths were similar between 'FAES1307' and its parent, 'TAES 5309-12' in run two.

Considering flowering associated traits, 'FAES1307' consistently had shorter flag leaf heights; however, its height was not different from any entry in run one (Table 1). In run two, 'Emerald' had a shorter flag leaf height and 'BA 123' and 'SS-500' both had longer flag leaf heights. Flag leaf heights were always similar between 'FAES1307', 'Meyer', 'TAES 5309-12' and 'Zeon'. For flag leaf widths, there were few differences in run one. For both runs, 'FAES1307' only had similar leaf widths to 'BA 123'. For seed head height, 'FAES1307' was among the shorter entries in both runs. In both runs, 'FAES1307' was similar with its parent, 'TAES 5309-12', for seed head height. 'BA 123' was similar to 'FAES1307' with a short seed head in run one but was different in run two developing the tallest seed heads. 'SS-500' and 'Meyer' consistently produced taller seed heads. For culm length, 'FAES1307' was shorter in both runs compared to 'SS-500' and 'Meyer' and similar in both runs to 'Zeon' and 'TAES 5309-12'. 'BA 123' had shorter seed heads in the second run. For measurements of inflorescence widths, 'FAES1307' was among the narrower entries. It was not different in both runs from 'Meyer', and 'SS-500'. In run one 'FAES1307' had a greater inflorescence width than 'BA 123' and greater than 'TAES 5309-12' in run two. The inflorescence lengths of 'FAES1307' were similar to 'TAES 5309-12' in both runs. 'BA 123' and 'Zeon' had shorter lengths in run two while 'Meyer' and 'SS-500' had longer lengths in both runs compared to 'FAES1307'. Lastly, 'FAES1307' produced fewer spikelets per raceme than 'Meyer' and 'SS-500' and similar numbers of spikelets to 'Zeon', 'TAES 5309-12', and 'BA 123' for both runs of measurements.

The following are additional unique and distinguishing characteristics exhibited by 'FAES1307' when grown under the above greenhouse conditions:

Plant:

*Growth habit*.—A perennial plant that spreads by stolons and rhizomes, and produces a dense, medium textured turfgrass.

*Leaves*.—Leaf blade color adaxial leaf surface: 137B moderate olive green. Leaf blade color abaxial leaf surface: 137B moderate olive green. Attachment: Sheathing. Shape: Linear. Apex shape: Acute. Aspect: Semierect. Texture: Smooth with occasional fine hairs (upper surface); smooth (lower surface). Margins: Entire. Venation: Parallel. Leaf collar: Continuous and narrow. Ligule: Hairy. Auricle: None.

*Stolon color* (*in absence of light*).—N144A strong yellow green.

*Time of flowering*.—March-May in Gainesville, Fla.

*Floret size*.—2.3-2.4 mm.

*Floret shape*.—Elliptic.

*Floret color*.—1st glume: N77D greyish reddish purple. 2md glume: Absent. Palea: 157D greenish white. Lemma: 157D greenish white.

*Stigma shape*.—Feathery.

*Ovary*.—Size: 0.5-0.7 mm. Color: NN155B pale white.

*Caryopses*.—Size: 0.8-1.0 mm. Shape: Oval. Color: Pale yellow 161C.

Inflorescence: Produces primarily terminal spike-like racemes, with spikelets on short appressed pedicels. The spikelets generally occur singularly appressed against the slender rachis.

*Culm stalk color*.—138A moderate yellow green.

*Glume color*.—79D moderate purple.

*Stigma color*.—NN155B white.

*Anther* (*fresh*) *color*.—155A pale yellow green.

Turf Quality, Shade Tolerance, Spring Green-Up, and Fall Color Retention Comparison of 'FAES1307' to Commercial and Experimental Genotypes 'FAES1307' was evaluated in field trials conducted in Citra, Fla., Jay, Fla., Auburn, Ala., and College Station, Tex. Plots at these locations were established using rooted plugs. In these trials, turfgrass fall color retention, turfgrass spring green-up, and turfgrass quality were evaluated using the industry recognized 1 to 9 visual rating scale established by the National Turfgrass Evaluation Program (NTEP) in which "9" indicates "best" and "1" indicates "poorest." Multiple ratings were taken over several years until the end of 2016.

As shown in Table 2, 'FAES1307' was compared to the experimental varieties 'FAES1312', 'FAES1313' and 'FAES1319', and commercial varieties 'SS-500', 'Meyer' (not patented), and 'Zeon' (U.S. Plant Pat. No. 13,166). 'FAES1307' was superior to 'SS-500' and 'Meyer', but was not different from 'Zeon' in mean turfgrass fall color retention at the College Station, Tex. and Citra, Fla. locations. 'FAES1307' was superior to 'SS-500' and 'Zeon' in spring turfgrass green-up at the Auburn, Ala. location, but was similar to 'Meyer'. 'FAES1307' was superior to 'SS-500', 'Meyer', and 'Zeon' in turfgrass spring green-up at the Citra, Fla. location. The 2015 annual average for turfgrass quality of 'FAES1307' was superior to 'SS-500' and 'Meyer', but was similar to 'Zeon' at the Citra, Fla. location. The 2015 average for turfgrass quality of 'FAES1307' was similar to 'SS-500', 'Zeon' and 'Meyer' at the Jay, Fla. location.

Long term performance of a new turfgrass under multiple environments is most indicative of merit. 'FAES1307' was entered into several multi-year trials and with the NTEP 2013 National Zoysiagrass Trial. The 2013 NTEP Zoysiagrass Trial was planted at 17 locations throughout the USA and included 35 entries and utilized the zoyiagrass varieties 'SS-500', 'Meyer' (not patented), and 'Zeon' (U.S. Plant Pat. No. 13,166) as check varieties. Maintaining quality under shade conditions is an important trait. 'FAES1307' was grown under 70 percent shade for 3-years in a non-NTEP trial in Hague, Fla. and compared to 'SS-500'. Additionally, 'FAES1307' was compared to 'SS-500', 'Meyer', and 'Zeon' grown under shade in Riverside, Calif. as part of the NTEP Zoysiagrass Trial. Turfgrass quality under shade was measured on a 1 to 9 rating scale where "9" indicates the best turfgrass quality when grown in shade and "1" indicates the poorest turfgrass quality when grown in shade. Turfgrass quality ratings under shade from Hague, Fla. and Riverside, Calif. are shown in Table 3. Sod strength (Table 3) was measured as the pounds of force required to break a piece of sod. Percent severity of large patch (*Rhizoctonia solani* anastomosis group 2-2 LP) was visually rated in the Arkansas and Florida NTEP trials as the percentage of a plot exhibiting symptoms of large patch disease.

In the 2016 multi-location NTEP Zoysiagrass Trial, 'FAES1307' had higher average turfgrass quality ratings than either 'SS-500' or 'Meyer', but was not different from 'Zeon'. When grown under 70% shade Hague, Fla., 'FAES1307' had superior turfgrass quality compared to 'SS-500' and 'FAES1313' and 'FAES1319' but was not different from 'FAES1312'. In the shade trial at Riverside, Calif., 'FAES1307' was superior in turfgrass quality to 'SS-500', 'Meyer', and 'Zeon', but was not different from 'FAES1313' and 'FAES1319'. Measurements of sod strength from the experiment at NCSU showed that 'FAES1307' was superior to 'SS-500' and 'Meyer' and to 'FAES1312', 'FAES1313' and 'FAES1319'.

Figure 3:
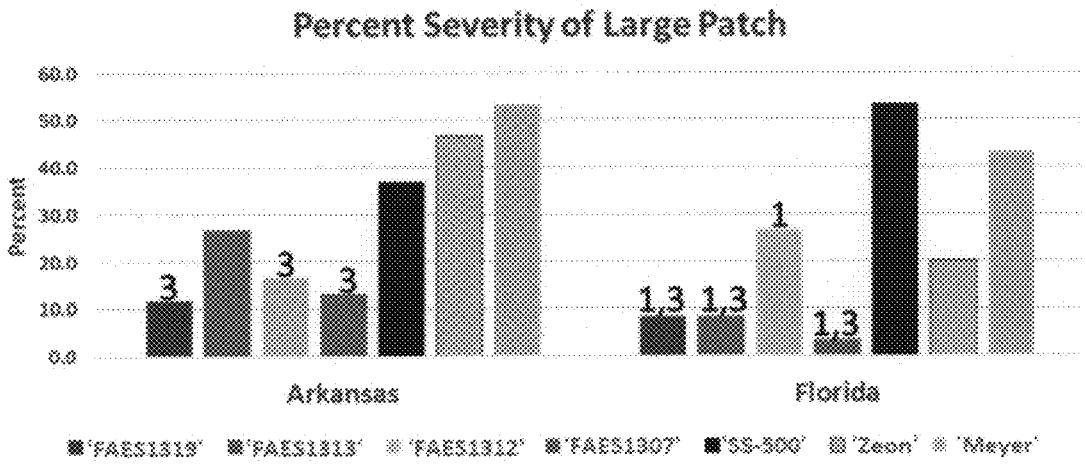
FIG. 3—Shows percent severity of large patch disease (*Rhizoctonia solani*) in 2017 of 'FAES1307' in comparison to commercial and experimental zoysiagrass genotypes from the 2013 National Turfgrass Evaluation Program zoysiagrass trial. Numbers over a column indicate that the column entry was significantly different from the entry number as determined by the following: 1=entry better than 'SS-500', 2=entry better than 'Zeon', and 3=entry better than 'Meyer'.

Disease Response Comparison of 'FAES1307' to Commercial and Experimental Genotypes Disease response is an important characteristic for new turfgrass cultivars. As illustrated in FIG. 3, 'FAES1307' had significantly lower severity of large patch disease compared to 'SS-500' and 'Meyer' when evaluated in Florida. 'FAES1307' had lower disease severity than 'Meyer' when evaluated in Arkansas.

TABLE 1

Morphological comparisons between 'FAES1307', its parents and commercial cultivars.

| Entry | Canopy Height (cm) | Stolon Number | Stolon Length (cm) | Leaf Length (cm) | Leaf Width (cm) | Flag Leaf Height (cm) |
|---|---|---|---|---|---|---|
| | | | Run One | | | |
| 'FAES1307' | 4.6 | 14.3 | 39.5 | 1.6 | 0.18 | 3.5 |
| '5309-12' | 5.9 | 6.7 | 24.5 | 1.7 | 0.24 | 3.7 |
| 'BA123' | 6.1 | 5.7 | 21.3 | 1.9 | 0.10 | 3.7 |
| 'Emerald' | 5.3 | 3.3 | 13.7 | 1.8 | 0.13 | 4.3 |
| 'SS-500' | 6.4 | 1.8 | 14.1 | 2.0 | 0.30 | 3.7 |
| 'Meyer' | 7.2 | 5.2 | 27.2 | 2.5 | 0.33 | 3.7 |
| 'Zeon' | 5.2 | 4.8 | 20.0 | 1.8 | 0.13 | 3.4 |
| lsd (0.05)§ | 0.8 | 3.9 | 10.6 | 0.5 | 0.04 | 0.7 |
| | | | Run Two | | | |
| 'FAES1307' | 10.0 | 33.8 | 36.9 | 3.8 | 0.20 | 7.6 |
| '5309-12' | 13.3 | 24.6 | 41.3 | 3.3 | 0.21 | 8.4 |
| 'BA123' | 13.7 | 14.4 | 31.1 | 2.6 | 0.10 | 13.7 |
| 'Emerald' | 8.9 | 13.4 | 24.5 | 2.3 | 0.14 | 4.9 |
| 'SS-500' | 14.0 | 16.4 | 35.4 | 6.1 | 0.31 | 9.9 |
| 'Meyer' | 14.8 | 14.0 | 44.8 | 4.2 | 0.31 | 9.7 |
| 'Zeon' | 12.0 | 32.0 | 38.6 | 4.2 | 0.13 | 5.8 |
| lsd (0.05)§ | 1.9 | 11.8 | 12.5 | 1.3 | 0.03 | 2.1 |

| Entry | Flag Leaf Width (cm) | Inflorescence Traits: Height (cm) | Culm Length (cm) | Width (mm) | Length (mm) | Spikelet Number |
|---|---|---|---|---|---|---|
| | | | Run One | | | |
| 'FAES1307' | 0.12 | 5.8 | 2.4 | 2.4 | 13.2 | 13.3 |
| '5309-12' | 0.14 | 5.8 | 2.2 | 2.1 | 14.5 | 15.4 |
| 'BA123' | 0.10 | 5.2 | 1.7 | 1.7 | 10.3 | 9.8 |
| 'Emerald' | 0.10 | 7.5 | 3.7 | 2.7 | 17.1 | 18.3 |
| 'SS-500' | 0.14 | 8.3 | 5.0 | 2.5 | 24.0 | 27.4 |
| 'Meyer' | 0.20 | 9.6 | 5.1 | 2.5 | 31.7 | 31.4 |
| 'Zeon' | 0.10 | 6.4 | 3.3 | 3.2 | 13.9 | 16.1 |
| lsd (0.05)§ | 0.05 | 1.4 | 0.8 | 0.7 | 3.1 | 4.2 |
| | | | Run Two | | | |
| 'FAES1307' | 0.7 | 11.1 | 6.7 | 1.6 | 20.2 | 15.7 |
| '5309-12' | — | 11.5 | 5.2 | 1.2 | 19.0 | 15.0 |
| 'BA123' | 0.4 | 16.2 | 3.6 | 1.5 | 15.5 | 15.6 |
| 'Emerald' | 0.1 | 7.6 | 5.9 | 2.1 | — | 18.0 |
| 'SS-500' | 1.7 | 15.8 | 10.3 | 1.7 | 34.8 | 31.3 |
| 'Meyer' | 0.1 | 15.0 | 10.0 | 1.7 | 37.7 | 29.9 |

TABLE 1-continued

Morphological comparisons between 'FAES1307', its parents and commercial cultivars.

| | | | | | | |
|---|---|---|---|---|---|---|
| 'Zeon' | 0.1 | 7.9 | 5.2 | 1.8 | 16.3 | 16.3 |
| lsd (0.05)§ | 0.6 | 2.5 | 1.9 | 0.3 | 3.4 | 4.7 |

§Numbers within a column that differed by the lsd (least significant difference) value are significantly different ($p \leq 0.05$).

TABLE 2

Turfgrass fall color retention, spring green-up, and seasonal average quality of selected zoysiagrass genotypes.

| | Turfgrass Fall Color Retention | | Turfgrass Spring Green-Up | | Yearly Average Turfgrass Quality | |
|---|---|---|---|---|---|---|
| Entry | College Station, TX | Citra, FL | Auburn, AL | Citra, FL | Citra, FL | Jay, FL |
| 'FAES1307' | 6.3 | 5.8 | 8.4 | 8.0 | 5.5 | — |
| 'FAES1312' | 5.7 | 5.3 | 8.7 | 6.8 | 5.7 | 6.4 |
| 'FAES1313' | 7.7 | 6.3 | 7.3 | 7.2 | 5.8 | 6.4 |
| 'FAES1319' | 7.0 | 6.3 | 7.2 | 6.8 | 5.6 | 6.6 |
| 'SS-500' | 4.3 | 2.7 | 6.6 | 6.0 | 4.1 | 6.2 |
| 'Meyer' | 3.3 | 2.7 | 8.4 | 3.0 | 3.1 | 6.3 |
| 'Zeon' | 7.3 | 5.0 | 6.6 | 5.3 | 4.6 | 5.9 |
| lsd (0.05)§ | 1.5 | 1.4 | 1.3 | 1.1 | 0.8 | 0.6 |

§Numbers within a column that differed by the lsd (least significant difference) value are significantly different ($p \leq 0.05$).

TABLE 3

Turfgrass shade tolerance, sod strength, and overall turfgrass quality evaluations of selected zoysiagrass genotypes.

| | Shade Tolerance | | | Overall 2016 NTEP |
|---|---|---|---|---|
| Variety | Riverside, CA | Hague, FL | Sod Strength Raleigh, NC | Turfgrass Quality 11 Locations |
| 'FAES1307' | 6.3 | 5.5 | 189 | 6.3 |
| 'FAES1312' | 4.7 | 6.0 | 77 | 6.6 |
| 'FAES1313' | 5.7 | 2.0 | 89 | 6.4 |
| 'FAES1319' | 5.7 | 4.5 | 61 | 6.7 |
| 'SS-500' | 4.3 | 3.0 | 40 | 5.7 |
| 'Meyer' | 4.0 | — | — | 5.3 |
| 'Zeon' | 4.7 | — | 73 | 6.4 |
| lsd (0.05)§ | 0.8 | 1.0 | 17 | 0.3 |

§Numbers within a column that differed by the lsd (least significant difference) value are significantly different ($p \leq 0.05$).

What is claimed is:

1. A new and distinct variety of zoysiagrass plant named 'FAES1307', as illustrated and described herein.

* * * * *